US00PP26717P2

(12) United States Plant Patent
Nishikawa

(10) Patent No.: US PP26,717 P2
(45) Date of Patent: May 10, 2016

(54) ***CALENDULA* PLANT NAMED '20123-72D'**

(50) Latin Name: *Calendula officinalis*
Varietal Denomination: 20123-72D

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 51 days.

(21) Appl. No.: 14/121,836

(22) Filed: Oct. 23, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Penny J. Aguirre

(57) ABSTRACT

A new cultivar of *Calendula* plant, '20123-72D', that is characterized by its strong, compact, creeping plant habit, its inflorescences with double ray florets that are yellow in color on the upper surface and orange in color on the lower surface and disk florets that are deep greyed-red in color, its long flowering time; blooming for 9 months from spring into winter in Noordwijkerhout, The Netherlands, its very high tolerance to powdery mildew, and its very high tolerance to heat and cold, withstanding temperatures below −20° C. in the winter and its ability to be readily propagated by stem cuttings.

2 Drawing Sheets

Botanical classification: *Calendula officinalis.*
Variety denomination: '20123-72D'.

CROSS REFERENCE TO RELATED APPLICATIONS

This application is co-pending with U.S. Plant Patent Applications filed for plants derived from the same breeding program that are entitled *Calendula* Plant Named '20124-30D' (U.S. Plant patent application Ser. No. 14/120,524)* and *Calendula* Plant Named '20123-107D' (U.S. Plant patent application Ser. No. 14/121,837).

BACKGROUND OF THE INVENTION

The present invention relates to a new and distinct cultivar of *Calendula* plant, botanically known as *Calendula officinalis* '20123-72D' and will be referred to hereinafter by its cultivar name, '20123-72D'. The new cultivar of *Calendula* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of vegetatively propagated *Calendula* plants with low-growing and well-spreading growth habits combined with long flowering periods and a unique range of flower colors.

'20123-72D' was selected in the Inventor's trial garden in 2012 as a single unique plant from amongst the seedlings derived from self-crossing an unnamed plant (not patented) from the Inventor's breeding program, ref. code 20122-7D, in 2012.

Asexual propagation of the new cultivar was first accomplished by stem cuttings in summer of 2012 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish '20123-72D' as a unique cultivar of *Calendula.*

1. '20123-72D' exhibits a strong, compact, creeping plant habit.
2. '20123-72D' exhibits inflorescences with double ray florets that are yellow in color on the upper surface and orange in color on the lower surface and disk florets that are deep greyed-red in color.
3. '20123-72D' exhibits a long flowering time; blooming for 9 months from spring into winter in Noordwijkerhout, The Netherlands.
4. '20123-72D' exhibits very high tolerance to powdery mildew.
5. '20123-72D' exhibits very high tolerance to heat and cold, withstanding temperatures below −20° C. in the winter.
6. '20123-72D' is readily propagated by stem cuttings.

'20123-72D' can best be compared to plants of the *Calendula* seed strain 'Alice'. 'Alice' differs from '20123-72D' in having flowers that are larger in size, in having a shorter four month long blooming period, in being poorly branched, in being susceptible to powdery mildew, heat, and cold, and in being propagated by seed. '20123-72D' can also be compared to the co-pending *Calendula* cultivars '20124-30D' and '20123-107D'. '20124-30D' differs from '20123-72D' in having larger inflorescences with ray florets that are yellow in color with orange tips on both surfaces and disk florets that are yellow in color. '20123-107D' differs from '20123-72D' in having inflorescences with ray florets that are more orange in color with more rounded tips and in having disk florets that are yellow in color. There are no cultivars of *Calendula officinalis* that are vegetatively propagated known to the Inventor other than those bred by the Inventor. The Inventor has no records on the characteristics of the parent plant.

BRIEF DESCRIPTION OF THE DRAWINGS

The accompanying colored photographs illustrate the overall appearance and distinct characteristics of the new *Calendula*. The plant in the photograph about seven months in age as grown outdoors in a 13-cm container in Noordwijkerhout, The Netherlands.

The photograph in FIG. 1 provides a side view of the plant habit of '20123-72D' in bloom.

Figure 1:
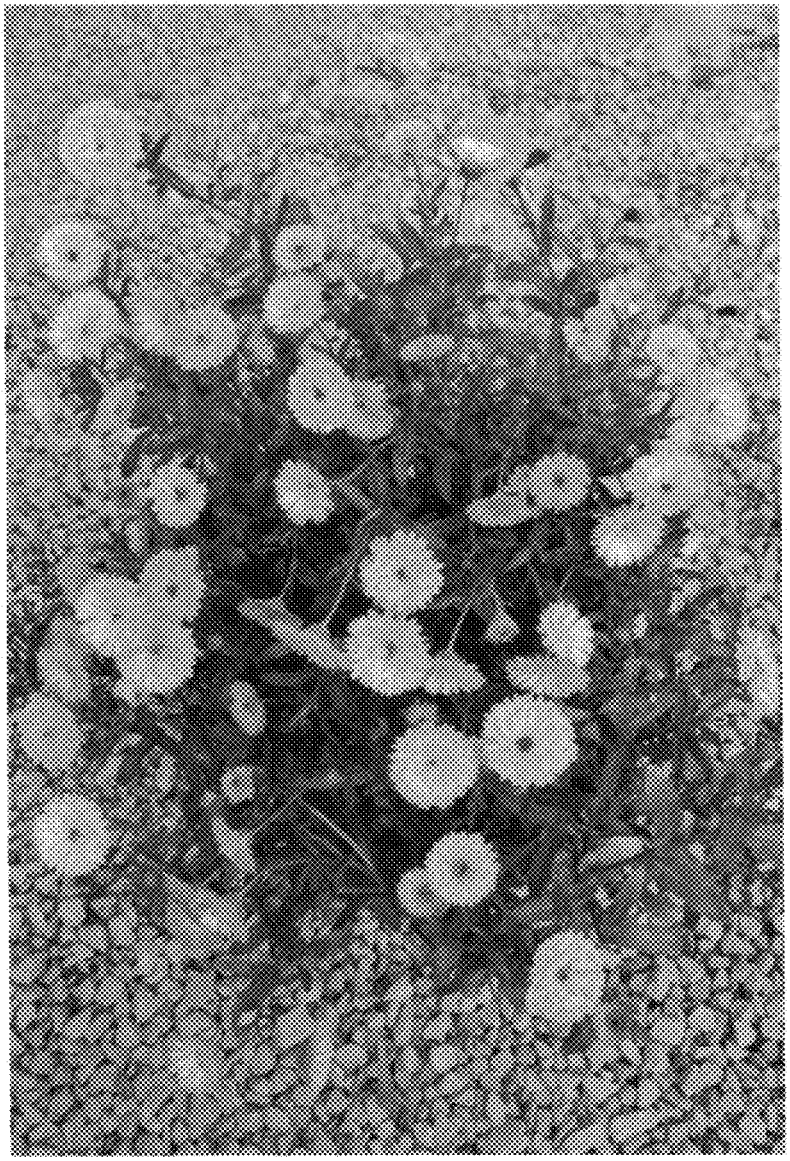
Figure 2:
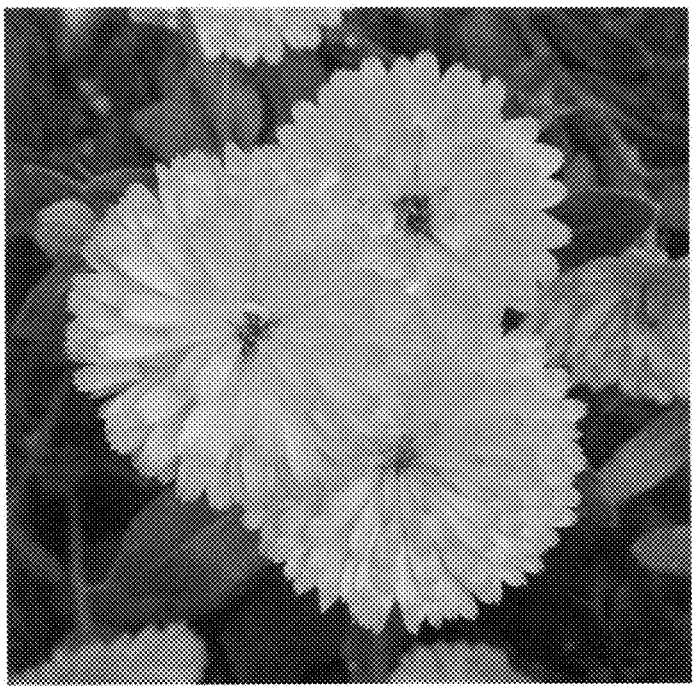

The photograph in FIG. 2 provides a close-up view of a flower of '20123-72D'.

Figure 3:
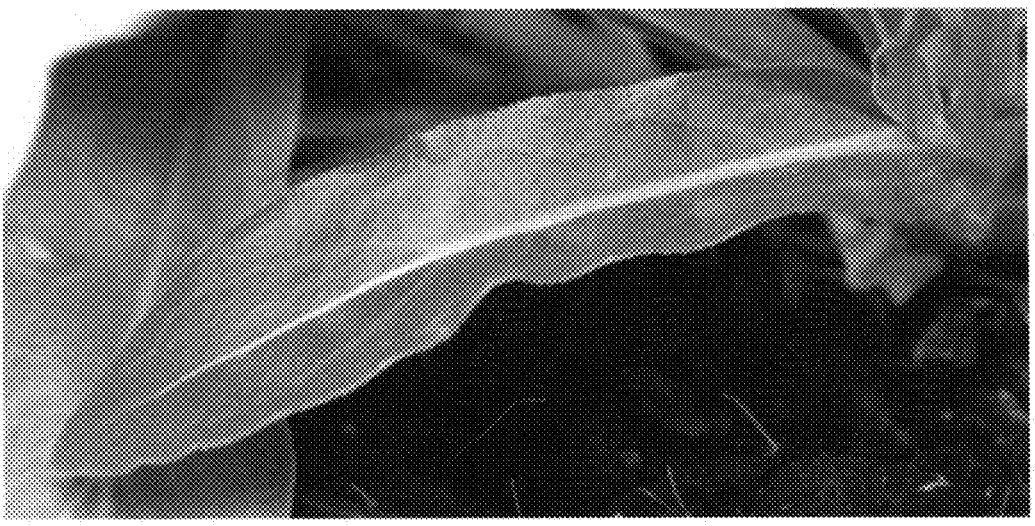

The photograph in FIG. 3 provides a close-up view of the foliage of '20123-72D'.

The colors in the photographs may differ slightly from the color values cited in the detailed botanical description, which accurately describe the colors of the new *Calendula*.

DETAILED BOTANICAL DESCRIPTION

The following is a detailed description of five month-old plants of the new cultivar as grown outdoors in 13-cm containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of nine-months from spring into winter in Noordwijkerhout, The Netherlands.

*Plant type*.—Herbaceous perennial.

*Plant habit*.—Strong, compact, creeping plant habit.

*Height and spread*.—Reaches about 17.5 cm in height and 20.5 cm in diameter (5 month-old plants).

*Cold hardiness*.—Observed to be hardy to U.S.D.A. Zone 7.

*Diseases*.—Has been shown to have a very high tolerance to powdery mildew caused by *Podosphaera xanthii*.

*Root description*.—Fine and fibrous roots.

*Propagation*.—Softwood stem cuttings.

*Growth habit*.—Moderately vigorous.

*Rooting*.—Roots initiate and fill a 104-cell plug in about 3 weeks and the liner will fully develop in a 9-cm container in 6 weeks.

Stem description:

*Shape*.—Rounded.

*Stem color*.—143B.

*Stem size*.—An average of 11.5 cm in length and 0.4 cm in diameter.

*Stem strength*.—Strong.

*Stem aspect*.—Lateral stems grow in an average angle of 50° (0°=horizontal) to the main stem.

*Stem surface*.—Moderately glossy, sparsely covered with very short soft hairs; to small to measure and NN155D in color.

*Stem number*.—5 lateral branches.

*Internode length*.—Average of 1.8 cm in length.

*Branching*.—Stems grow from base.

Foliage description:

*Leaf shape*.—Narrow oblanceolate.

*Leaf division*.—Simple.

*Leaf base*.—Truncate, decurrent.

*Leaf apex*.—Obtuse.

*Leaf venation*.—Pinnate, color: upper surface; 147C, lower surface; 144B.

*Leaf margins*.—Entire, undulate, moderately covered with very short strigose hairs; average length of 0.04 cm and NN155D in color.

*Leaf attachment*.—Sessile.

*Leaf arrangement*.—Alternate.

*Leaf size*.—Average of 8.7 cm in length and 2.6 cm in width.

*Leaf color*.—Young upper surface; N137B, young lower surface; 137C, mature upper surface; N137B, mature lower surface; 147B.

*Leaf surface*.—Upper and lower surfaces are moderately rough to the touch and moderately covered with very short strigose hairs 0.03 cm in length and NN155D in color, upper surface is moderately glossy and lower surface is very slightly glossy.

*Petioles*.—No petioles present, leaves are decurrent.

Inflorescence description:

*Inflorescence type*.—Terminal capitulum consisting of disc and ray florets.

*Inflorescence number*.—Average of 1 per lateral stem.

*Inflorescence fragrance*.—None.

*Inflorescence aspect*.—Straight on top of stem.

*Inflorescence longevity*.—A few weeks.

*Inflorescence size*.—Average of 1.6 cm in height and 4.8 cm in diameter.

*Inflorescence buds*.—Average of 2 per lateral stem, broad ovate to globular in shape, average of 1.2 cm in length and 12 cm in diameter, color; 138A to 138B, apex is 24A to 25B.

*Receptacle*.—Inverted triangular in shape, 3 mm in height, 5 mm in diameter and 157D in color.

*Peduncle*.—3 cm in length and 2 mm in diameter, terminal peduncle is straight on top of stem, other peduncles in an average angle of 30° to stem, moderate strength, very sparsely covered with short soft hairs; average of 0.7 mm in length and NN155D in color.

*Involucral bracts*.—Average of 24 per inflorescence, arranged in 2 rows, lanceolate in shape, narrowly acute apex, cuneate base, margin entire, 9 mm in length, 2 mm in width, upper surface is glabrous and glossy, lower surface is matte and densely covered with very short pubescence; average length is 0.5 mm and NN155C in color, color; upper surface 138A, lower surface 137B.

Ray florets (pistillate):

*Number*.—Average of 150.

*Arrangement*.—Rotate, 7 whorls.

*Shape*.—Oblanceolate.

*Aspect*.—Slightly upright at the base, held in an average angle of 35°, whole ray floret near horizontal.

*Size*.—Average of 2 cm in length and 4 mm in width.

*Petal apex*.—Praemorse, typically with 3-notches.

*Petal base*.—Narrow cuneate.

*Petal margins*.—Entire.

*Petal surface*.—Upper surface is slightly glossy, glabrous and velvety, lower surface is matte and glabrous.

*Petal color*.—When opening upper surface; 13B to 13C, base 14A, tip 24A, when opening lower surface; 25A, base 16A, when fully open upper surface; color between 13C and 15A, base 23A, tip 24A, when fully open lower surface; 25A, base 23A.

Disk florets (perfect): Glabrous and glossy surfaces, spirally placed on disc average of 5 disc florets per inflorescence, shape is tubular, upper $1/6^{th}$ of tepals free, tip is acute, fused into tube, entire margin, average of 6 mm in length and 2 mm in width, color of upper and lower surfaces when opening; 178A, base 2B to 2C, color of fully opened upper surface; 178A, base is 2B to 2C, color of fully opened lower surface; 9C, base 150D.

Reproductive organs:

*Gynoecium*.—1 pistil per ray floret, 4.5 mm in length, stigma unequal decurrent and 15A in color, style is 2 mm in length and 9B in color, ovary 150D in color.

*Androecium*.—5 stamens, filament length is 2 mm and 154D in color, anther is linear in shape, 5 mm in length and 153D in color, pollen amount is moderate in quantity and 23A in color.

*Fruit and seed*.—No fruits or seeds have been observed to date.

It is claimed:

1. A new and distinct variety of *Calendula* plant named '20123-72D' as described and illustrated herein.

* * * * *